(12) United States Patent
Menhardt

(10) Patent No.: US 6,661,869 B2
(45) Date of Patent: Dec. 9, 2003

(54) IMAGE RECONSTRUCTION USING MULTIPLE X-RAY PROJECTIONS

(75) Inventor: Wido Menhardt, Los Gatos, CA (US)

(73) Assignee: Cedara Software Corp., Ontario (CA)

(*) Notice: Subject to any disclaimer, the term of this patent is extended or adjusted under 35 U.S.C. 154(b) by 0 days.

(21) Appl. No.: 10/260,634

(22) Filed: Sep. 30, 2002

(65) Prior Publication Data

US 2003/0118151 A1 Jun. 26, 2003

Related U.S. Application Data

(63) Continuation of application No. 09/742,048, filed on Dec. 20, 2000, now Pat. No. 6,470,070.

(51) Int. Cl.$^7$ .............................................. G01N 23/04
(52) U.S. Cl. ........................................ 378/62; 378/98.3
(58) Field of Search ....................... 378/4, 8, 62, 98.2, 378/98.3, 901

(56) References Cited

U.S. PATENT DOCUMENTS

| | | |
|---|---|---|
| 4,101,961 A | 7/1978 | Reiber |
| 4,422,146 A | 12/1983 | Yamaguchi et al. |
| 4,630,203 A | 12/1986 | Szirtes |
| 4,672,651 A | 6/1987 | Horiba et al. |
| 4,875,165 A | 10/1989 | Fencil et al. |
| 5,065,435 A | 11/1991 | Oe |
| 5,107,838 A | 4/1992 | Yamaguchi |
| 5,274,549 A | 12/1993 | Almasi |
| 5,421,331 A | 6/1995 | Devito et al. |
| 5,435,310 A | 7/1995 | Sheehan et al. |
| 5,442,672 A | 8/1995 | Bjorkholm et al. |
| 5,457,754 A | 10/1995 | Han et al. |
| 5,570,430 A | 10/1996 | Sheehan et al. |
| 5,588,033 A | 12/1996 | Yeung |
| 5,601,084 A | 2/1997 | Sheehan et al. |
| 5,617,459 A | 4/1997 | Makram-Ebeid et al. |
| 5,669,382 A | 9/1997 | Curwen et al. |
| 5,699,799 A | 12/1997 | Xu et al. |
| 5,734,739 A | 3/1998 | Sheehan et al. |
| 5,848,114 A | 12/1998 | Kawai et al. |
| 5,871,019 A | 2/1999 | Belohlavek |
| 5,889,524 A | 3/1999 | Sheehan et al. |
| 5,903,664 A | 5/1999 | Hartley et al. |
| 6,031,374 A | 2/2000 | Epstein et al. |
| 6,038,466 A | 3/2000 | Haselhoff |
| 6,047,080 A | 4/2000 | Chen et al. |
| 2003/0013953 A1 * | 1/2003 | Mistretta ............... 600/425 |

OTHER PUBLICATIONS

Niki, N. et al: "3D imaging of blood vessels using X–ray rotational angiographic system", Nuclear Science Symposium and Medical Imaging Conference, 1993., 1993 IEEE Conference Record. San Francisco, CA, USA. Oct. 31–Nov. 6, 1993, New York, NY. USA, IEEE pp. 1873–1877.

(List continued on next page.)

*Primary Examiner*—David V. Bruce
(74) *Attorney, Agent, or Firm*—Pearne & Gordon LLP

(57) ABSTRACT

A method for reconstructing two and three dimensional images of objects using X-ray image projections and iterative reconstruction techniques is provided. More specifically, the method provides an image of the object to be corrected. Two or more X-ray absorbance profiles of the image are obtained along two or more different projection directions. These profiles are compared with the corresponding absorbance profiles of the object substantially filled with an X-ray contrast agent and, based on this comparison, the image is corrected using the iterative reconstruction techniques. Before each iteration the pixels of the image are updated so that if the absorbance value of the pixel is below a preselected value then the pixel is set to 0, otherwise the pixel is set to the absorbance value corresponding to the concentration of the X-ray contrast agent within the object. The iteration stops when the difference between the absorbance profiles of the image and the object falls below a preselected value.

17 Claims, 3 Drawing Sheets

OTHER PUBLICATIONS

Andersen A H: "Algebraic Reconstruction in CT From Limited Views", IEEE Transactions of Medical Imaging, IEEE Inc., New York, NY, US. vol. 8, No. 1, Mar. 1, 1989, pp. 52–53.

Kawata Y et al.: "Three-dimensional imaging of blood vessels using cone-beam CT", Proceedings of the International Conference on Image Processing (ICIP), Austin, Nov. 13–16, 1994, Los Alamitos, IEEE Comp. Soc. Press, US, vol. 3 Conf. 1, pp. 140–144.

Patent Abstracts of Japan, vol. 2000, No. 14, Mar. 5, 2001 & JP 2000 325340 A (GE Yokogawa Medical Systems Ltd), Nov. 28, 2000.

Patent Abstracts of Japan, vol. 1996, No. 01, Jan. 31, 1996 & JP 07 239933 A ((Toshiba Medical Eng Co Ltd; other: 01), Sep. 12, 1995.

Harold Sandler, M.D. and Harold T. Dodge, M.D., Experimental and Laboratory Reports—The use of single plane angiocardiograms for the calculation of left ventricle volume in man, AM.HEARTJ, vol. 75, No. 3, Mar. 1968, pps. 325–334.

Kak and Slarney, Algebraic Reconstruction Algorithms—Principles of Computerized Tomographic Imaging, IEEE press 1988, pps. 275–296.

Shigeru Eiho, Shigeru Yamada, Michiyoshi Kuwahara, Image Processing of X-ray Left Ventricular Cineangiocardiograms and Displays of Cardiac Functions, Japanese J. of Soc. of Instrument and Control Engineers, vol. 19, No. 10, 1980, pps. 923–936.

\* cited by examiner

IMAGE RECONSTRUCTION USING MULTIPLE X-RAY PROJECTIONS

This is a continuation of U.S. patent application Ser. No. 09/742,048, filed Dec. 20, 2000 now U.S. Pat. No. 6,470,070.

The present invention relates to methods for reconstructing two and three dimensional images of objects using X-ray image projections and algebraic reconstruction techniques.

BACKGROUND OF THE INVENTION

X-ray imaging is widely used to image internal organs for diagnostic purposes and to assist health practitioners during therapeutic interventions. For example, this technique has found many applications in cardiology including intra ventricular interventional cardiac procedures such as Direct Myocardial Revascularization and electro physiological mapping and ablation.

In order to extract useful structural information from X-ray irradiation of an object, the projections data must often be extensively processed using image reconstruction techniques. Such image reconstruction techniques are well-known in the art and include for example, algorithms known as ART (Algebraic Reconstruction Techniques). A good introduction to these concepts can be found in Principles of Computerized Tomographic Imaging, by Kak and Slaney, IEEE Press, 1988. Using these techniques, X-ray tomographic images can be obtained by irradiating the object to be examined from a multiplicity of directions and processing the information from each of the projections to reconstruct the image of the object.

Image reconstructions based on ART often require many projections from different angles (often more than 100) to obtain good quality images. As a result, acquisition times are long and necessitate the immobilization of the patient for prolonged periods to minimize positional errors. Furthermore, the long acquisition times may be prohibitive for emergency procedures and may reduce the availability of the apparatus.

Methods have been devised to reduce the number of projections required to obtain satisfactory images. One such method is disclosed in U.S. Pat. No. 4,672,651 wherein two X-ray projections of an object are obtained from which an initial image of the object is corrected by a relaxative procedure. More specifically, the shape of the object is modified or corrected in accordance with individual data values in the projection images for the two directions, thereby producing a corrected shape. Eiho et al. (Japanese J. of Soc. of Instrument and Control Engineers Vol. 19 No. 10, Pages 923–936, 1980) disclose a similar method for image reconstruction using two projections. However, these methods are generally limited to ellipsoid objects and require extensive computational time.

A further method has been described in U.S. Pat. No. 5,442,672 that uses two X-ray projections to tomographically reconstruct images of objects in baggages. The method is based on multiplicative algebraic reconstruction techniques (MART) wherein successive slices of the object are projected. This method requires that the value of each pixel in the image intercepted by a given X-ray, be adjusted to the average density of the object along the path of the X-ray. However, the method is somewhat limited by the heterogony of the object's densities which have to be estimated. Accordingly, a number of constraints have to be applied pertaining to the characteristics of the objects such as density and spacial continuity for example. Furthermore, the acquisition of several slices within each projection and their processing for image reconstruction may be time consuming.

In view of the state of the art, it would be desirable to provide a method requiring few projections and rapid computational calculations to effect the correction of the projections data.

SUMMARY OF THE INVENTION

The present invention relates to a method for reconstructing the image of an object using at least two X-ray projections.

According to one aspect of the present invention, there is provided a method of constructing an image of an object using at least two X-ray absorbance profiles. The method comprises the steps of; a) filling the object to be imaged with an X-ray agent, the X-ray agent attenuating X-rays; b) generating at least two one-dimensional X-ray absorbance profiles with respect to a pre-selected plane of the object by irradiating the agent-filled object with X-rays from at least two directions; c) producing a two-dimensional image by back-projecting the above at least two one-dimensional X-ray absorbance profiles; d) transforming the two-dimensional image into a two-dimensional binary image; e) forward-projecting the two-dimensional binary image into at least two one-dimensional projections, wherein the one-dimensional X-ray absorbance profiles and the one-dimensional projections correspond to each other; f) estimating a difference between each X-ray absorbance profile and each corresponding projection; and g) producing a corrected two-dimensional image by normalizing the difference throughout the two-dimensional binary image.

According to another aspect of the present invention, there is provided a method of constructing the image of an object using at least two X-ray absorbance profiles. The method comprises the steps of; a) filling the object to be imaged with an X-ray agent, the X-ray agent attenuating X-rays; b) generating at least two one-dimensional X-ray absorbance profiles by irradiating the age rays from at least two directions, each profile having a plurality of profile elements, each of which corresponds to a certain X-ray path; c) producing a first image by back-projecting the above at least two one-dimensional X-ray absorbance profiles, wherein the first image includes a plurality of picture elements, each picture element having each respective X-ray absorbance value; d) transforming the first image into a binary image; e) forward-projecting the binary image into at least two one-dimensional projections, wherein the one-dimensional X-ray absorbance profiles and projections correspond to each other; f) estimating a difference between each X-ray absorbance profile and each corresponding projection; and g) to produce a corrected image.

According to another aspect of the present invention, there is provided an apparatus for constructing an image of an object using at least two X-ray absorbance profiles. The apparatus comprises the steps of; a) means for filling the object to be imaged with an X-ray agent, the X-ray agent attenuating X-rays; b) means for generating at least two one-dimensional X-ray absorbance profiles with respect to a pre-selected plane of the object by irradiating the agent-filled object with X-rays from at least two directions; c) means for producing a two-dimensional image by back-projecting the above at least two one-dimensional X-ray absorbance profiles; d) means for transforming the two-dimensional image into a two-dimensional binary image; e) means for forward-projecting the two-dimensional binary image into at least two one-dimensional projections, wherein the one-dimensional X-ray absorbance profiles and the one-dimensional projections correspond to each other; f) means for estimating a difference between each X-ray absorbance profile and each corresponding projection; and g) means for producing a corrected two-dimensional image by normalizing the difference throughout the two-dimensional binary image.

According to the present invention is also provided a method for reconstructing an image of an object using at least two single plane X-ray projections, the method comprising the steps of; irradiating said object with X-rays from at least two directions; detecting said X-rays transmitted through said object to define at least two projection mask X-ray absorbance profiles; substantially uniformly filling the object with an X-ray contrast agent; irradiating said contrast agent-filled object with X-rays from at least two directions; detecting said X-rays transmitted through said contrast agent-filled object to define at least two live X-ray projection absorbance profiles; subtracting said mask profiles from said live profiles to define a final absorbance profile for each projection; providing a first image to be corrected; updating said image by setting the absorbance value to 0 for all picture elements having an absorbance below a preselected threshold value and by setting all other picture elements to the absorbance value corresponding to the concentration of the X-ray contrast agent within the object; forward projecting the updated image into said at least 2 planes of projection along said at least two directions to obtain X-ray absorbance profiles of said image to be corrected; calculating the difference between the absorbance profiles of the object and of the image to be corrected; correcting the updated image using iterative reconstruction techniques; repeating the correction until the difference between the current absorbance profiles and the object absorbance profiles is less than a selected value; displaying the image.

In an embodiment of the present invention a method is provided to reconstruct images of ellipsoid objects using 2 projections. In a further embodiment, a method is provided to reconstruct the image of non-ellipsoid objects using 3 or more projections.

BRIEF DESCRIPTION OF THE DRAWINGS

These and other features of the invention will become more apparent from the following description in which reference is made to the appended drawings wherein.

DESCRIPTION OF PREFERRED EMBODIMENT

The method of this invention will be described with reference to the image reconstruction of a 2-dimensional section of a 3-dimensional object but as will be obvious to those of skill in the art the instant method can readily be applied to a 3-dimensional image reconstruction.

Figure 1A:
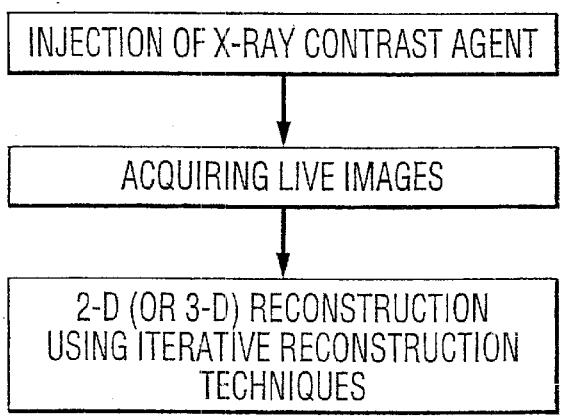
FIG. 1A is a flow chart diagram of the steps involved in the image reconstruction of the instant invention.

In FIG. 1A, a flow chart diagram outlines the steps leading to the production of a 2-dimensional (2-D) image of a section of an object using the method of the instant invention. The 2-D image is reconstructed starting from at least two single planes 1 dimensional (1-D) X-ray image projections of a section of an object. First, an X-ray contrast agent is injected in the object by a selected means. Then, a series of X-ray absorbance profiles, with the contrast agent substantially uniformly filling the object, is acquired for each projection. Finally, the 1-D profiles thus obtained are reconstructed into 2-D images by a method that will be described below.

Figure 1B:
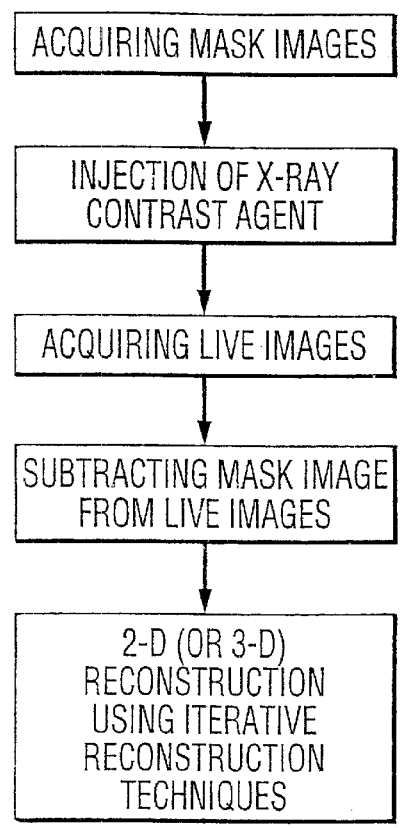
FIG. 1B is a flow chart diagram of the steps involved in the image reconstruction of the instant invention in the embodiment using mask images.

In another embodiment as outlined in FIG. 1B, a series of mask X-ray absorbance profiles for each projection is acquired without X-ray contrast agent prior to injecting the contrast agent. In this embodiment, the 2-D image of a section of an object is then reconstructed as follows: A series of mask absorbance profiles for each projection is first acquired without X-ray contrast agent. Then, an X-ray contrast agent is injected in the object by a selected means followed by the acquisition of a series of live X-ray absorbance profiles with the contrast agent substantially uniformly filling the object. The mask profiles are then subtracted from the corresponding live profiles. Finally, the 1-D profiles thus obtained are transformed into 2-D images.

Figure 2:
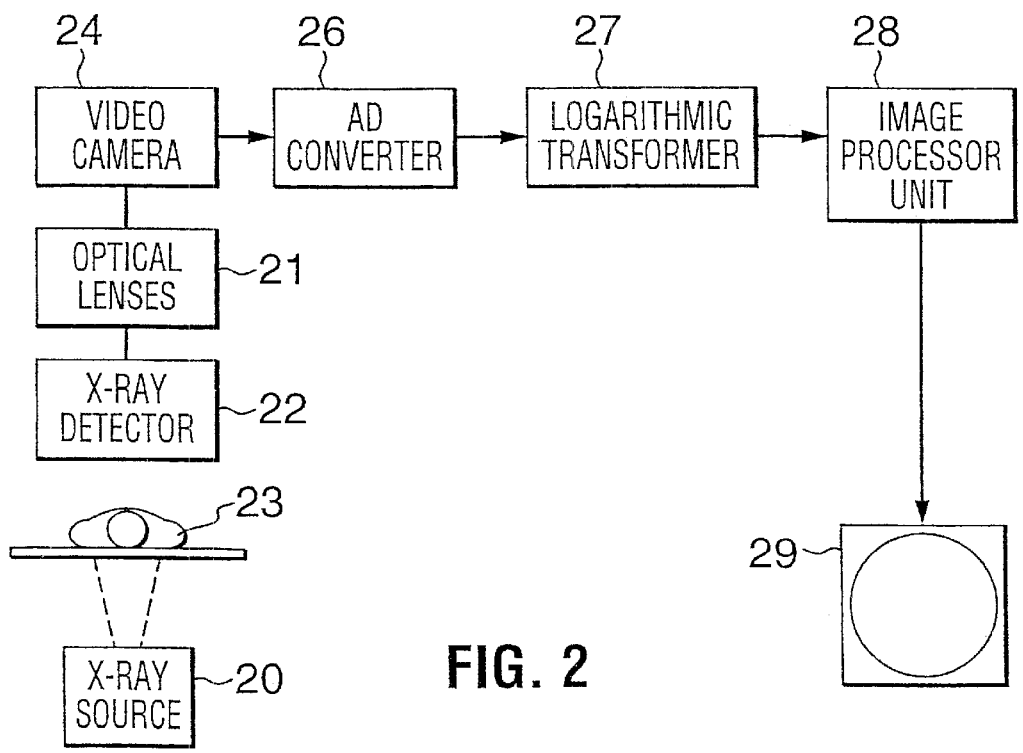
FIG. 2 is a schematic representation of the imaging system.

X-ray sensitive films can be used to record X-rays transmitted through the object being imaged. However, in a preferred embodiment of this invention, the intensity of X-rays transmitted through an object is recorded on an image intensifier screen which can be a fluorescent screen although other type of screens can be used and are well known in the art. Images acquired on fluorescent screens are referred to as fluorograms. These screens allow the rapid acquisition of multiple frames, an essential characteristic to image moving object such as the heart. The following is a description of a typical imaging system and is schematically represented in FIG. 2 for explanatory purposes and is not intended to restrict the scope of the invention. Other arrangements as would be obvious to one skilled in the art are also considered to be within the scope of the invention. The X-ray source 20 generates parallel X-rays upon application of a high voltage. The X-ray detector 22, which is an image intensifier, detects X-rays transmitted through the object (an organ for example) 23. The detector 22 also functions to electron-multiply the detected X-rays for conversion into an optical image. It is preferable that the size of the X-ray detecting surface of the X-ray detector 22 can cover that part of the X-rays which are transmitted through the object 23. A TV camera 24 is coupled to the X-ray detector 22 through an optical lens 21 to convert the optical image into an electrical signal. The TV camera 24 is controlled in a well known manner by a TV camera controller which in turn amplifies suitably the electrical output signal of the TV camera 24. The amplified signal is converted into a digital value by an A/D converter 26, and a logarithmic transformer 27 transforms the digital output of the A/D converter 26 into a logarithmic value which represents X-ray absorbance of the object 23. The logarithmic output of the logarithmic transformer 27 is applied to an image processor unit 28 which converts the signal into an image displayed on screen 29. Alternatively, the A/D conversion may be carried out after the logarithmic conversion. Such an imaging system can acquire images at approximately 20 screens/second.

Figure 3:
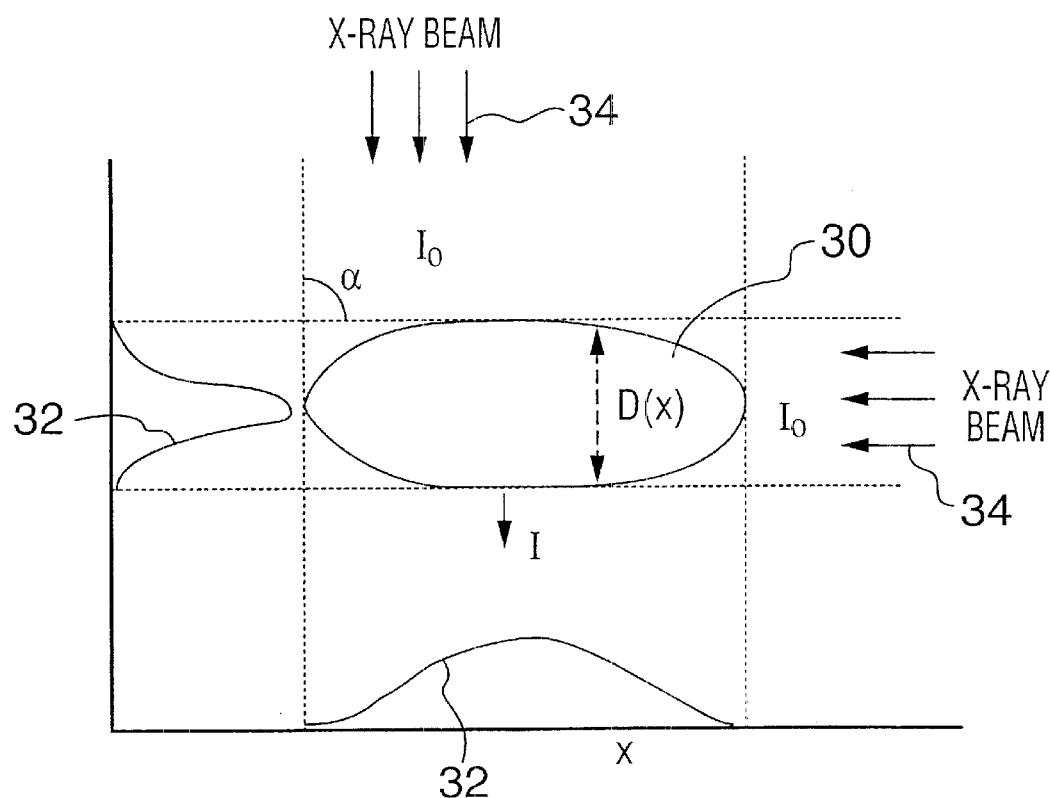
FIG. 3 illustrates for the purpose of example only, the projection profiles of an ellipsoid object.

The method for reconstructing the 2-D image of a section of an object starting with a single plane 1-D X-ray absorbance profile will now be described with reference to FIG. 3.

For the purpose of example only, the method will be described using an ellipsoid object generally described at 30. First, at least two 1-D absorbance profiles 32 are obtained by irradiating the object with X-rays 34 having intensity $I_o$ from two different directions separated by an angle α. The X-rays are partly absorbed within the object by the X-ray contrast agent and exit the object with a reduced intensity I. In a preferred embodiment of the invention, the concentration of the X-ray contrast agent within the object is assumed to be constant. The ratio $I_o/I$ is logarithmically proportional to the path length of the X-rays within the ventricle according to the following relationship:

$$Log\ I_o/I = \epsilon c D(x) \tag{1}$$

Thus the logarithm of the ratio of the intensity of the incoming X-rays to the intensity of the transmitted X-rays (the absorbance) at a position (x) in the projection is proportional to the absorptivity coefficient ε of the contrast agent, the concentration c of the contrast agent within the object and the distance D(x) travelled by the X-ray within the object. The image of the object is then reconstructed using the projections thus obtained. Although the X-ray beam in FIG. 3 is depicted as being parallel, it will appreciated that the method of the instant invention can also be applied to cone-shaped X-ray beam.

In the method of the instant invention the reconstruction is based on iterative reconstruction techniques algorithms which involve the projection of the image to be reconstructed onto hyperplanes. These techniques are well known in the art and will be briefly described. The hyperplanes are defined by the sum of the contribution of each pixel to the absorbance of a particular X-ray path (the ray-sum). The image to be corrected is projected onto the first hyperplane (first ray-sum) and a correction of the absorbance value of each pixel is calculated. The correction is given by the difference between the absorbance value of the object for a given X-ray path and the calculated ray-sum of the same X-ray path based on the image to be corrected. The difference is then normalized to the number of pixels intercepted by the X-ray path and added to the current estimation. The iteration proceeds until the difference between the current image projection and the projection of the object falls below a predetermined value. In a preferred embodiment the difference is taken as the mean square difference. Essentially the algorithm projects, ray by ray, the initial image to be corrected into the planes of projection and this projection is compared with the projection of the object. A correction based on this difference is backprojected to define a new image and the iteration repeats. In a variation of the above-described algorithm, all the rays within one projection are projected simultaneously instead of one by one and the correction is based on the assumption that the image is a continuous function of absorbance instead of being composed of discrete pixels. The algorithms may include, but are not limited to, Algebraic Reconstruction Techniques (ART) and Simultaneous Algebraic Reconstruction Techniques (SART). A good description of these algorithms can be found in Principles of Computerized Tomographic Imaging, by Kak and Slaney, IEEE Press, 1988,pp275–296. The method of the instant invention is implemented as an improvement of these algorithms.

Radon's theorem stipulates that an infinite number of projections is required to obtain an infinite resolution of the image. In practice, using the methods of the prior art described above, a good quality image reconstruction can be obtained using a large number of projections, which can often be in excess of several hundreds, and a large number of iterations. However, such a large number of projections still represents a major impediment to rapidly obtaining image reconstructions. It is therefore an object of the instant invention to provide a method in which the number of projections and iterations required to obtain a good reconstruction is substantially reduced. In particular, the instant invention is based on the discovery that by setting, before every iteration, all pixels in the image having an absorbance value below a certain threshold to zero and all other pixels to the absorbance value corresponding to the concentration c of the contrast agent within the object according to equation 1, it is possible to greatly reduce the number of projections and iterations necessary to obtain a reconstructed image of a quality sufficient for surgical guidance for example. The details of the method of the instant invention will now be described.

In one embodiment of the instant method the initial image to be corrected is obtained as follows: First, two or more single plane X-ray projections of the object are obtained. The absorbance value at each position x in each projection is then backprojected along the direction of the forward projection into an area defined by the intersection of the two or more backprojected absorbance profiles. The absorbance of each position x is equally distributed within the intersection area along the direction of the projection. The absorbance from all backprojections in the intersection area is then integrated to yield a gray scale image. Initial images to be corrected can also be obtained by other means, such as estimating the shape of the object and the concentration of X-ray contrast agent within the object based on previous knowledge. Other means of obtaining the initial image, as would be obvious to those skilled in the art, are also contemplated to be within the scope of the invention.

The absorbance value of each pixel in the initial image is then compared to a predetermined threshold value. All pixels below this value are set to 0 and the remaining pixels are set to the absorbance value corresponding to the concentration of the X-ray contrast agent. This results in a tresholded binary image. In a further embodiment, the pixels with a value equals to or greater than the threshold value can be set to the threshold value. The thresholded image is forward projected into the two or more plane of projections and the absorbance profiles are compared to the absorbance profiles of the object. The image is corrected using the algorithms described above and the difference between the profiles of the image to be corrected and that of the actual object may further be scaled by a relaxation factor, having a value between 0 and 1, before being backprojected into the image. A new grayscale image is thus obtained. This completes one iteration. Optionally, a limited number of iterations may be performed without thresholding the image prior to performing iterations with thresholding. In one embodiment, approximately 20 iterations without thresholding are performed before including the thresholding in the iterations. It will be appreciated that the number of iterations without thresholding may vary depending on the shape of the object, the number of projections used, the limit for the convergence or any other parameters as would be obvious to one skilled in the art. The choice of the threshold value and the methods to obtain it will be described below.

At the beginning of each iteration the pixels in the image are updated using a threshold value that is either constant or variable throughout the image reconstruction. By variable it is meant that a new threshold is used for each iteration. The iterations are repeated until the difference between the absorbance value of the current projections and the absorbance value of the object projections is below a selected value. This selected value should be large enough to allow convergence of the algorithm but should be small enough so that the final (converged) image conforms to the object. In a preferred embodiment, the difference is the mean square difference. In a further embodiment the mean square difference is less than 0.0005 and preferably less than 0.0001. The thresholding of the image allows the algorithm to converge to a solution with fewer iterations and fewer projections than if no threshold is applied.

Figure 4:
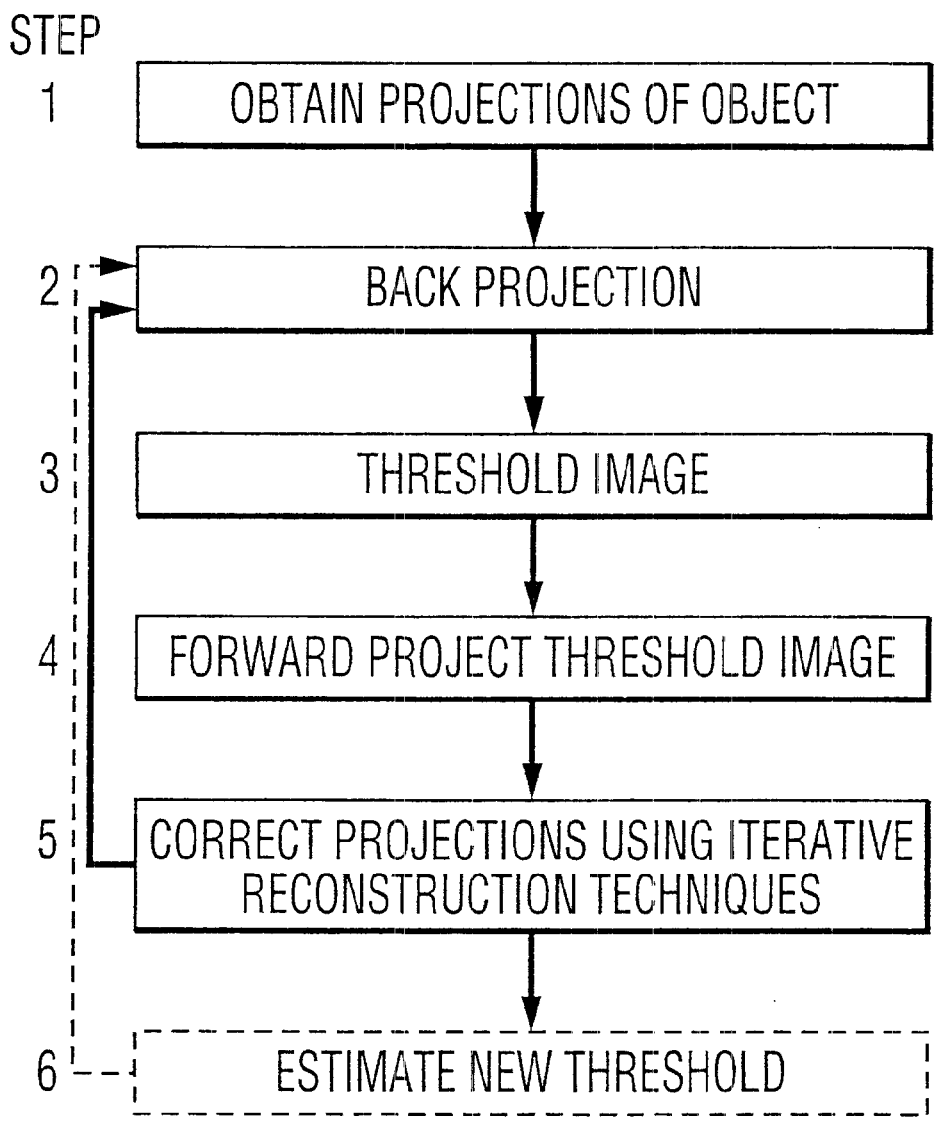
FIG. 4 is a flow chart diagram of the steps involved in the image reconstruction using either a constant or a variable threshold value.

With reference to FIG. 4, the steps in the method of the instant invention using either the fixed threshold or the variable threshold will now be described. In step 1, projections of the object are obtained. In step 2 the projections are backprojected to obtain the initial image to be corrected. In step 3 the pixels in the image below the threshold value are set to 0 and the pixels having absorbance values equal to or greater than the threshold value are set to the absorbance value corresponding to the concentration of the X-ray contrast agent within the object. In step 4 the thresholded image is forward projected into the two or more plane of projection. In step 5 the projections of step 4 are corrected as described above. The corrected projections are back-projected (step 2) and the iteration repeats starting at step 2.

In the embodiment using the variable threshold there is an additional step (step 6) in which a new threshold is estimated using the corrected projections of step 5. This new threshold value is then used to threshold the image at step 3.

In one embodiment of the instant method the threshold value is selected to be between 0 and the absorbance value corresponding to the concentration of the X-ray contrast agent within the object. In a further embodiment the threshold value is chosen to be substantially identical to the absorbance value corresponding to the concentration of the X-ray contrast agent within the object. In the embodiment wherein the threshold is held constant during iterations, the constant threshold value is preferably chosen to be within 1% of the actual concentration of the X-ray contrast agent within the object. However, other values depending on the convergence limit, the shape of the object, the number of projections or other parameters, as would be obvious to those skilled in the art, may also be used. If the density of the object is not known, it must somehow be estimated. Several methods for estimating the density will now be given but other methods, as would be obvious to one skilled in the art, are also contemplated to be within the scope of the invention.

In one aspect of the invention the density of the object, provided the object is ellipsoid, can be estimated by obtaining two projections of the object angularly separated by 90° with one of the projection being obtained with the X-ray beam substantially parallel to either the major or the minor axis. The width of one projection is equal to the distance travelled by the X-ray within the object that correspond to the maximum absorbance value in the other projection. Using equation 1, the concentration can then be obtained.

In a further aspect, the threshold can be determined by adjusting its value until the total absorbance of the image matches the total absorbance of the object. The total absorbance of the object can be determined from any projection by integrating its absorbance profile. Optionally, the integrated absorbance of many projections can be averaged. A threshold is then chosen that produces an image having a total absorbance substantially similar to the total absorbance of the object, for instance by increasing the threshold until the absorbance of the image equals that of the object.

One potential problem with determining the threshold by matching the absorbance is that the total absorbance versus threshold curve for an image is not a simple linear relation. As the threshold increases, fewer pixels contribute to the image so the total absorbance tends to decrease. However, as the threshold value increases, the remaining pixels, which are adjusted to the threshold value, exhibit a higher absorbance value and this tends to increase the total absorbance. Thus the absorbance versus threshold curve is not in general strictly decreasing and there may be more than one threshold that gives the correct total absorbance in the embodiment where the threshold is adjusted before each iteration. Another problem is that the shape of the curve will change as the iterations increase and as the threshold changes. However, only threshold values allowing convergence will be retained. If the total absorbance vs threshold curves are known it may be possible to limit the search of the threshold to certain regions of these curves to increase the likelihood of convergence.

In a further aspect, the threshold value for each iteration is chosen from a pixel of the image. Preferably a pixel is chosen for which the absorbance remains stable during convergence.

In yet a further aspect, the threshold of the image to be corrected can be modified until the area of the thresholded image matches that of the object. The area of the object may be estimated from the two or more initial projections provided that the shape of the object is known. For example, if the object is ellipsoid and that two 90° projections are obtained with one projection substantially parallel to the either the major or the minor axis, the width of the two projections correspond to the length of the axes thus providing the necessary parameters to calculate the area of the object. The area of objects exhibiting other shapes may also be calculated based on geometric relationships and orientation of the projections.

The number of projections required to obtain a good quality image using the method of the instant invention depends on the shape of the object. In one embodiment of the instant method, objects having at least one axis of symmetry and no gaps in any lines that is perpendicular to the axis of symmetry can be reconstructed using two projections. It is preferred that the angle between the two projections is 90° and that one of the two projections should be substantially parallel to one of the axis of symmetry of the object. By substantially parallel it is meant that the projection should make an angle of approximately 10° or less with the axis of symmetry. Objects having more complicated shapes can be reconstructed using 3 or more projections. The optimal angle between the projections to achieve the best reconstruction may depend on the shape of the object. However, simple convex shapes without concave features can be reliably reconstructed by 3 projections separated by 45° using the method of the instant invention. Adding one more projection improves accuracy and helps to reconstruct more complicated shapes that can include discontinuities and concave features.

Although the previous description refers to the reconstruction of 2-D images of sections of an object, 3-D reconstructions are considered to be within the scope of the instant invention. As would be obvious to one skilled in the art at least two 2-D X-ray projections of an object can be obtained with each projection at least covering the entire surface of the object in the direction of the X-ray beam. The backprojection of these 2-D absorbance profiles will intersect to form a 3-D image to be corrected. The reconstruction can be effected using the method described above for 2-D images.

For example, it is contemplated that the method of this invention can be used to image the left ventricle of a mammalian heart. However, any organ or object amenable to X-ray imaging can be reconstructed using the instant invention. In a preferred embodiment two projections of the left ventricle, angularly separated by 90° with one of the projection substantially parallel to the long axis (parasternal axis), are obtained. It will be appreciated that the injection of an X-ray contrast agent can be performed before acquiring mask images so long as the mask images are acquired before the contrast agent reaches the organ.

The live images are preferentially obtained while substantially no contrast agent is outside of the object being imaged. In one embodiment of the instant invention this can be accomplished, for acquiring single plane 2-D X-ray images of the left ventricle, by injecting the contrast agent intravenously (IV) and obtaining first pass images. For the purpose of this description first pass images means acquiring X-ray images immediately after the contrast agent has entered the left ventricle and before the contrast agent is substantially ejected from the ventricle at the end of the cardiac cycle. In a further embodiment, images of the left ventricle can be obtained by injecting the contrast agent by intra cardiac route (IC) and obtaining images before a substantial amount of the agent has been ejected from the ventricle at the end of the cardiac cycle. Other methods of X-ray contrast agent administration are also contemplated in the instant invention. The method will depend on the organ or tissue being imaged as would be obvious to one skilled in the art and may include but are not limited to intramuscular (IM) and intra arterial (IA) routes. X-ray contrast agent are well known in the art and include but are not limited to iodine-containing compounds.

In the case where the object is the left ventricle the concentration of the X-ray contrast agent may be obtained by the following method: The concentration c represents the number of absorbing contrast agent particles per unit volume. Equation 1 can then be rewritten as $$\text{Log } I_o/I = \varepsilon \frac{\# \text{ absorbing particles}}{V} D(x, y) \qquad (2)$$

or $$\text{Log } I_o/I = \varepsilon \frac{\# \text{ absorbing particles}}{S} \qquad (3)$$

where S represents unit surface and V unit volume. Thus by adding the absorbance (Log $I_o/I$) over the entire surface of the projection image and dividing by $\varepsilon$ the total number of absorbing particles of the contrast agent can be obtained. The concentration is then calculated by dividing the number of particle by the volume of the ventricle. In one aspect of the invention the volume of the ventricle can be closely approximated by using the following formula (derived from Sandler H. and Dodge H. T., Am. Heart Journal, 1968:325–338):

$$V=8S^2/3\pi L \qquad (4)$$

where S is the surface of the 2-D projection image and L is the length of the principal axis of the ventricle obtained from the projection image.

In the method of the instant invention the quality of the reconstructed image in the presence of noise can be improved by increasing the convergence limit or by smoothing the image using techniques well known in the art. For example, if the object is assumed to be smooth in outline, smoothing of the output image by erosion/dilation methods can be used to further improve the image quality.

The present invention has been described with regard to preferred embodiments. However, it will be obvious to persons skilled in the art that a number of variations and modifications can be made without departing from the scope of the invention as described herein.

What is claimed is:

1. A method of constructing an image of an object using at least two X-ray absorbance profiles, the method comprising the steps of;
   a) filling the object to be imaged with an X-ray agent, the X-ray agent attenuating X-rays;
   b) generating at least two one-dimensional X-ray absorbance profiles with respect to a pre-selected plane of the object by irradiating said agent-filled object with X-rays from at least two directions;
   c) producing a two-dimensional image by back-projecting said at least two one-dimensional X-ray absorbance profiles;
   d) transforming said two-dimensional image into a two-dimensional binary image;
   e) forward-projecting said two-dimensional binary image into at least two one-dimensional projections, wherein said one-dimensional X-ray absorbance profiles and said one-dimensional projections correspond to each other;
   f) estimating a difference between each said X-ray absorbance profile and each corresponding projection; and
   g) producing a corrected two-dimensional image by normalizing said difference throughout said two-dimensional binary image.

2. The method according to claim 1, further comprising a step of repeating said step d) to g) using said corrected two-dimensional image until said difference is less than a pre-selected value.

3. The method according to claim 1, wherein said X-ray agent is substantially uniformly filled in the object to be imaged.

4. The method according to claim 1, wherein in said step d), picture elements of said two-dimensional binary image are set to zero or a certain pre-selected value.

5. The method according to claim 4, wherein said pre-selected value is an X-ray absorbance value corresponding to the concentration of the X-ray agent.

6. The method according to claim 1, further comprising steps of: before said step a), generating at least two one-dimensional mask X-ray absorbance profiles with respect to substantially the same plane of the object in said step b) by irradiating the object to be imaged with X-rays from substantially the same directions in said step b);
   before said step c), subtracting each said mask X-ray absorbance profile from each corresponding X-ray absorbance profile obtained in the step b) to define at least two final X-ray absorbance profiles, wherein said at least two final X-ray absorbance profiles are utilized in said step c).

7. A method of constructing the image of an object using at least two X-ray absorbance profiles, the method comprising the steps of;
   a) filling the object to be imaged with an X-ray agent, the X-ray agent attenuating X-rays;
   b) generating at least two one-dimensional X-ray absorbance profiles by irradiating said agent-filled object with X-rays from at least two directions, each profile having a plurality of profile elements, each of which corresponds to a certain X-ray path;
   c) producing a first image by back-projecting said at least two one-dimensional X-ray absorbance profiles, wherein said first image includes a plurality of picture elements, each picture element having each respective X-ray absorbance value;

d) transforming said first image into a binary image;

e) forward-projecting said binary image into at least two one-dimensional projections, wherein said one-dimensional X-ray absorbance profiles and projections correspond to each other;

f) estimating a difference between each said X-ray absorbance profile and each corresponding projection; and g) correcting said binary image using said difference to produce a corrected image.

8. The method according to claim 7, further comprising a step of repeating said step d) to g) using said corrected image until said difference is less than a certain pre-selected value.

9. The method according to claim 7, wherein said X-ray agent is substantially uniformly filled in the object to be imaged.

10. The method according to claim 7, wherein said step d) comprises steps of:

i) setting the absorbance value to zero for the picture elements having an absorbance value below a pre-selected threshold value:

ii) setting the absorbance value to a pre-selected absorbance value for the remaining picture elements.

11. The method according to claim 10, wherein said pre-selected absorbance value is an X-ray absorbance value corresponding to the concentration of said X-ray agent.

12. The method according to claim 10, wherein said pre-selected absorbance value is substantially the same as said a pre-selected threshold value.

13. The method according to claim 10, wherein said pre-selected threshold values substantially the same as the concentration of said X-ray agent.

14. The method according to claim 13, wherein said pre-selected threshold value is within 1% of the concentration of said X-ray agent.

15. The method according to claim 7, wherein said step f) includes a step of estimating a difference between each corresponding profile elements in said X-ray absorbance profiles and projections; and said step g) includes a step of normalizing each said difference to the number of picture elements intercepted by each corresponding X-ray path and adding the normalized value to corresponding picture elements in said binary image to produce said corrected image.

16. The method according to claim 7, further comprising steps of:

before said step a), generating at least two one-dimensional mask X-ray absorbance profiles by irradiating the object to be imaged with X-rays from substantially the same directions in said step b);

before said step c), subtracting said each mask X-ray absorbance profile from each corresponding one-dimensional X-ray absorbance profile obtained in the step b) to define at least two final X-ray absorbance profiles, wherein said at least two final X-ray absorbance profiles are utilized in said step c).

17. An apparatus for constructing an image of an object using at least two X-ray absorbance profiles, the apparatus comprising the steps of;

a) means for filling the object to be imaged with an X-ray agent, the X-ray agent attenuating X-rays;

b) means for generating at least two one-dimensional X-ray absorbance profiles with respect to a pre-selected plane of the object by irradiating said agent-filled object with X-rays from at least two directions;

c) means for producing a two-dimensional image by back-projecting said at least two one-dimensional X-ray absorbance profiles;

d) means for transforming said two-dimensional image into a two-dimensional binary image;

e) means for forward-projecting said two-dimensional binary image into at least two one-dimensional projections, wherein said one-dimensional X-ray absorbance profiles and said one-dimensional projections correspond to each other;

f) means for estimating a difference between each said X-ray absorbance profile and each corresponding projection; and g) means for producing a corrected two-dimensional image by normalizing said difference throughout said two-dimensional binary image.

* * * * *

UNITED STATES PATENT AND TRADEMARK OFFICE
CERTIFICATE OF CORRECTION

PATENT NO.     : 6,661,869 B2
DATED          : December 9, 2003
INVENTOR(S)    : Wido Menhardt It is certified that error appears in the above-identified patent and that said Letters Patent is hereby corrected as shown below:

Column 2,
Line 40, please delete "age rays", and insert therefor -- agent filled object with X-rays --.
Line 53, after "g)", please insert -- correcting the binary image using the difference --.

Column 11,
Line 33, please delete "values", and insert therefor -- value is --.

Signed and Sealed this

Sixteenth Day of March, 2004

JON W. DUDAS
*Acting Director of the United States Patent and Trademark Office*